United States Patent
Oliver et al.

(10) Patent No.: US 10,571,379 B2
(45) Date of Patent: Feb. 25, 2020

(54) COMPENSATED MECHANICAL TESTING SYSTEM

(71) Applicant: Nanomechanics, Inc., Oak Ridge, TN (US)

(72) Inventors: Warren C Oliver, Knoxville, TN (US); Sudharshan P Pardhasaradhi, Knoxville, TN (US); Michael P Drake, Knoxville, TN (US)

(73) Assignee: KLA-Tencor Corporation, Milpitas, CA (US)

( * ) Notice: Subject to any disclaimer, the term of this patent is extended or adjusted under 35 U.S.C. 154(b) by 210 days.

(21) Appl. No.: 15/089,923

(22) Filed: Apr. 4, 2016

(65) Prior Publication Data

US 2017/0284912 A1    Oct. 5, 2017

(51) Int. Cl.
*G01N 3/42* (2006.01)
*G01B 7/16* (2006.01)
*G01B 11/16* (2006.01)
*G01L 5/00* (2006.01)
(Continued)

(52) U.S. Cl.
CPC .............. *G01N 3/42* (2013.01); *G01B 7/22* (2013.01); *G01B 11/16* (2013.01); *G01L 5/0066* (2013.01); *G01L 25/00* (2013.01); *G01N 3/08* (2013.01); *G01N 2203/0202* (2013.01); *G01N 2203/06* (2013.01); *G01N 2203/0605* (2013.01)

(58) Field of Classification Search
None
See application file for complete search history.

(56) References Cited

U.S. PATENT DOCUMENTS

| | | | | |
|---|---|---|---|---|
| 284,827 | A * | 9/1883 | Elwell | F16F 15/14 74/57 |
| 4,036,048 | A * | 7/1977 | Webster | G01N 3/42 73/81 |

(Continued)

FOREIGN PATENT DOCUMENTS

| | | |
|---|---|---|
| JP | S60115830 A | 6/1985 |
| JP | 2003337094 A | 11/2003 |

OTHER PUBLICATIONS

"Ultra Nanoindentation Tester: New Generation of Thermal Drift Free Indentation," CSM Instruments Applications Bulletin No. 31, Feb. 2010.

(Continued)

*Primary Examiner* — Jill E Culler
(74) *Attorney, Agent, or Firm* — Luedeka Neely Group, P.C.; Mark Crockett; Rick Barnes

(57) ABSTRACT

A mechanical testing system having a frame, and a stage for holding a sample. An arm for pressing a tool against a surface of the sample. A primary actuator is connected to the frame and applies a primary force and drives the tool relative to the sample, thereby causing the frame to flex. A displacement sensor measures a displacement value comprised of two components, the first component including a distance traveled by the probe into the sample as the primary force is applied, and the second component including a measure of a degree of flex of the frame as the primary force is applied. A compensating actuator is connected to the frame and applies a compensating force that reduces the second component of the displacement value.

17 Claims, 4 Drawing Sheets

(51) Int. Cl.
G01L 25/00 (2006.01)
G01N 3/08 (2006.01)

(56) References Cited

U.S. PATENT DOCUMENTS

| | | | | |
|---|---|---|---|---|
| 4,699,000 | A * | 10/1987 | Lashmore | G01N 3/42 |
| | | | | 73/794 |
| 5,052,529 | A * | 10/1991 | Sutcliffe | F16F 6/00 |
| | | | | 188/378 |
| 5,975,508 | A * | 11/1999 | Beard | B60N 2/501 |
| | | | | 180/89.12 |
| 6,247,356 | B1 | 6/2001 | Merck et al. | |
| 7,107,159 | B2 | 9/2006 | German | |
| 7,246,517 | B2 | 6/2007 | Lee et al. | |
| 7,454,960 | B2 | 11/2008 | Ernst | |
| 7,568,381 | B2 | 8/2009 | Smith et al. | |
| 7,685,868 | B2 | 3/2010 | Woirgard et al. | |
| 8,074,497 | B2 | 12/2011 | Sawa et al. | |
| 8,302,456 | B2 | 11/2012 | Proksch | |
| 8,453,498 | B2 | 6/2013 | Warren et al. | |
| 2011/0270564 | A1 * | 11/2011 | Feero | G01L 25/00 |
| | | | | 702/104 |

OTHER PUBLICATIONS

Extended European Search Report for EP Application No. 17779590.3, dated Oct. 1, 2019, 11 pages.

* cited by examiner

COMPENSATED MECHANICAL TESTING SYSTEM

FIELD

This invention relates to the field of mechanical testing of materials. More particularly, this invention relates to a compensated measurement of the mechanical properties of a sample.

INTRODUCTION

Mechanical testing of materials involves applying a force to a sample of the material and measuring the resulting displacement of the material, or alternately imposing a displacement to the sample and measuring the force required to accomplish that displacement. In either case, the change in shape of the sample is an important parameter in such experiments.

The change in shape is measured by the displacement of one portion of the sample relative to another. Typically, this is accomplished by fixing the position of a reference point on the sample, such as by clamping the sample at that point, applying a force to the sample, and measuring the motion of a test point on the sample relative to the reference point. The intention is to hold the reference point as immobile as possible. However, the reference point will move if the clamping system is not infinitely rigid. If the measurement is made based on the assumption that the reference point is fixed, and it is not, then an error in the displacement measurement is introduced.

A specific example in which this concept applies is indentation testing. Indentation is a mechanical test that is often used for the measurement of hardness. It is performed by applying a known force for a known length of time through the tip of a probe that is in contact with the surface of a test sample, and measuring the surface area of the resulting indentation by imaging the residual impression. The force applied divided by the area yields the hardness of the sample. Other physical properties of the sample can be calculated from the data collected as the force is applied.

However, at smaller applied loads on hard surfaces, for example, the probe tip makes a smaller indentation. At a certain point, the imaging technology that is required to measure such small indentations can alternately become either a limiting factor or a cost-determining factor. Thus, in some systems, the measured displacement signal while the force is being applied and the known geometry of the tip are used to calculate the area of the indentation, which eliminates the need to image the indentation. This forms the basis for the field of instrumented indentation, which has many advantages over the traditional hardness measurements, especially at smaller length scales. In addition, measuring the displacement while the force is being applied enables the calculations of contact stiffness, which can be used to determine elastic modulus in addition to hardness.

As introduced above, the displacement measured by the displacement sensor includes two components. The first component is the displacement of the tip into the sample, which is of primary interest. The second component is the displacement or flexing of the testing frame, which is also referred to as the load frame. For some load frames, and especially at higher loads, this second component can be significant, and will deleteriously effect the measurement of the sample properties.

Theoretically, if a system were to be designed with a load frame having infinite stiffness, the contribution of the load frame to the displacement measured by the displacement sensor would be zero, which would yield a highly accurate instrumented indentation test. However, designing a system to have infinite load frame stiffness is challenging at best, given the many components that are typically incorporated into such a system, and the inherent lack of stiffness by design that such components exhibit.

What is needed, therefore, is a system that reduces issues such as those described above, at least in part.

SUMMARY

The above and other needs are met by mechanical testing system having a frame and a stage for holding a sample. An arm presses a tool against a surface of the sample. A primary actuator is connected to the frame and applies a primary force and drives the tool into the sample, thereby causing the frame to flex. A displacement sensor measures a displacement value comprised of two components, the first component including a distance traveled by the tool into the sample as the primary force is applied, and the second component including a measure of a degree of flex of the frame as the primary force is applied. A compensating actuator is connected to the frame and applies a compensating force that reduces the second component of the displacement value.

In various embodiments according to this aspect of the invention, the compensating actuator includes multiple compensating actuators disposed at different positions on the frame. In some embodiments the compensating actuator is disposed on an opposite side of the stage from the primary actuator. In some embodiments the primary actuator is at least one of electromagnetic, electrostatic, piezoelectric, hydraulic, mechanical, and pneumatic. In some embodiments the compensating actuator is at least one of electromagnetic, electrostatic, piezoelectric, hydraulic, mechanical, and pneumatic. In some embodiments the displacement sensor uses at least one of a capacitor and a laser to measure the displacement. In some embodiments the compensating force completely erases the second component of the displacement value. In some embodiments the compensating force corrects an apparent stiffness of the frame to about ten million newtons per meter.

According to another aspect of the invention there is described a method for testing at least one of a hardness and an elastic modulus of a sample by placing the sample to be tested on a stage that is supported by a frame. A primary actuator that is supported by the frame applies a primary force and drives a tool into a surface of the sample, thereby causing the frame to flex. A displacement value is measured with a displacement sensor. The displacement value is comprised of two components, the first component including a distance traveled by the tool into the sample as the primary force is applied, and the second component including a measure of the flex of the frame as the primary force is applied. A compensating force is applied with a compensating actuator that is connected to the frame, where the compensating force reduces the second component of the displacement value.

DRAWINGS

Further advantages of the invention are apparent by reference to the detailed description when considered in conjunction with the figures, which are not to scale so as to more clearly show the details, wherein like reference numbers indicate like elements throughout the several views, and wherein.

DESCRIPTION

Figure 1:
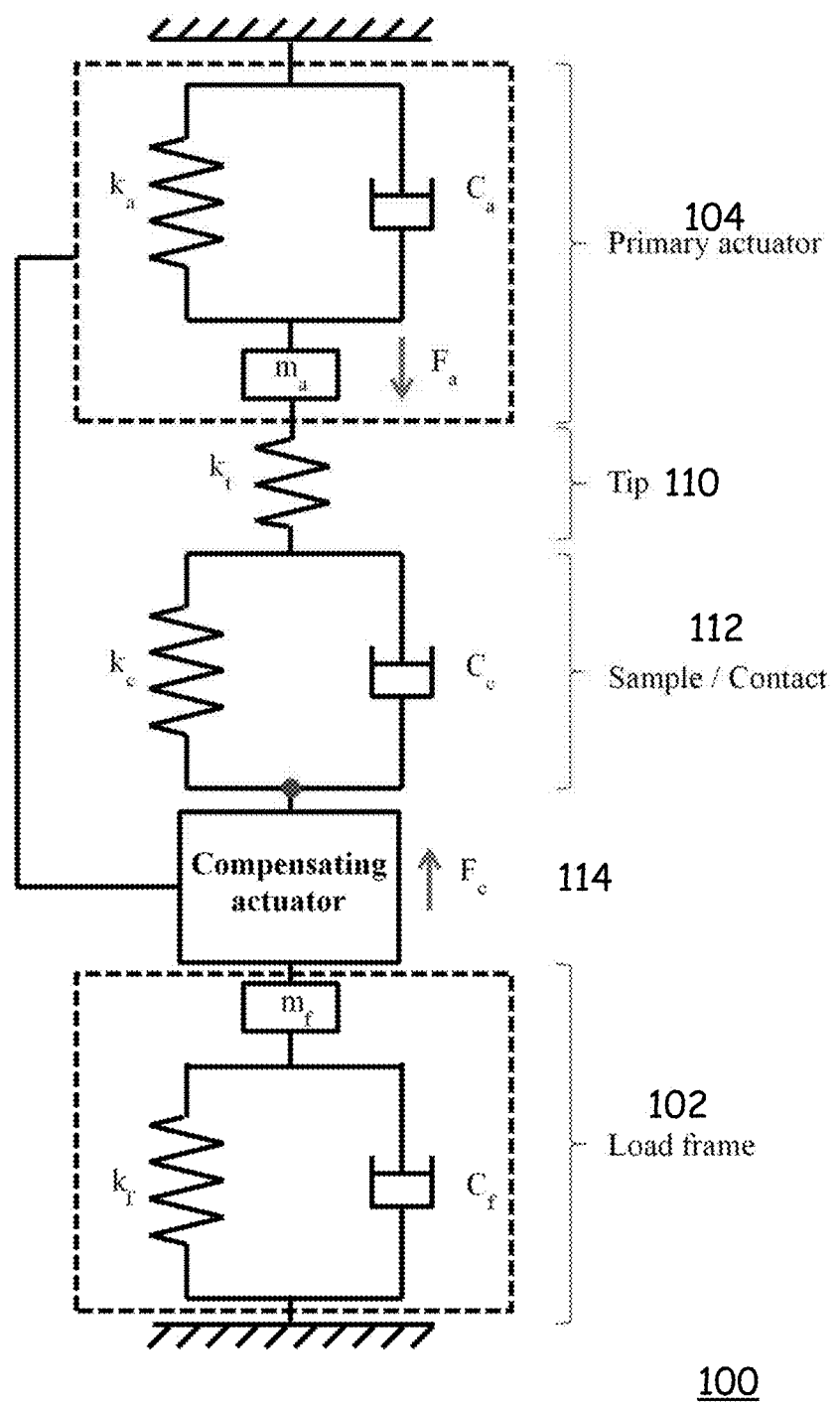
FIG. 1 is a schematic representation of mechanical testing system according to an embodiment of the present invention.

According to the embodiments of the present invention, load frame stiffness approaching infinite stiffness are achieved by maintaining a fixed (zero or non-zero) relative displacement between a reference point in the displacement sensor and a point on the sample, by using one or more compensating actuators. This is accomplished in the manner as described below.

With reference now to the figures there are depicted various embodiments of a mechanical testing system 100. The mechanical testing system 100 has a load frame 102 to which the various other components of the tester 100 are mounted. For example, a sample 112 is placed onto the tester 100, such as on a stage 113 that is useful for positioning various parts of the sample underneath a probe 108. On the end of the probe 108 is a tip 110 that is placed in contact with the upper surface of the sample 112 in a resting state with no exerted force, and the position of the tip 110 is measured, such as with a displacement sensor 106. This is the baseline position for the mechanical property measurement.

A primary actuator 104 starts to apply a load on the sample 112, by forcing the probe 108 down toward the sample 112, thereby pushing the tip 110 into the surface of the sample 112. The amount of force that is required to do this varies according to the hardness of the sample 112 and the depth of penetration. While the force is applied by the primary actuator 104, the displacement sensor 106 measures the distance from the baseline that the probe 108 has moved. The displacement sensor 106 can measure the displacement such as by using a variable capacitor or a laser, for example.

As introduced above, a portion of the movement measured by the displacement sensor 106 is due to the flexing of the frame 102, which occurs because of the resistance of the sample 112 to the penetration of the tip 110. The degree to which the frame 102 will flex is dependent upon a number of different factors, such as the construction of the frame 102 and the applied force, but is present to some degree or another in virtually all mechanical testing systems.

In addition to the flexing of the frame 102, other components of the system 100 might also flex or compress, further compounding the apparent error that arises by the displacement sensor 106 measuring a distance that is not entirely accounted for by the penetration of the tip 110 into the sample 112.

Figure 2:
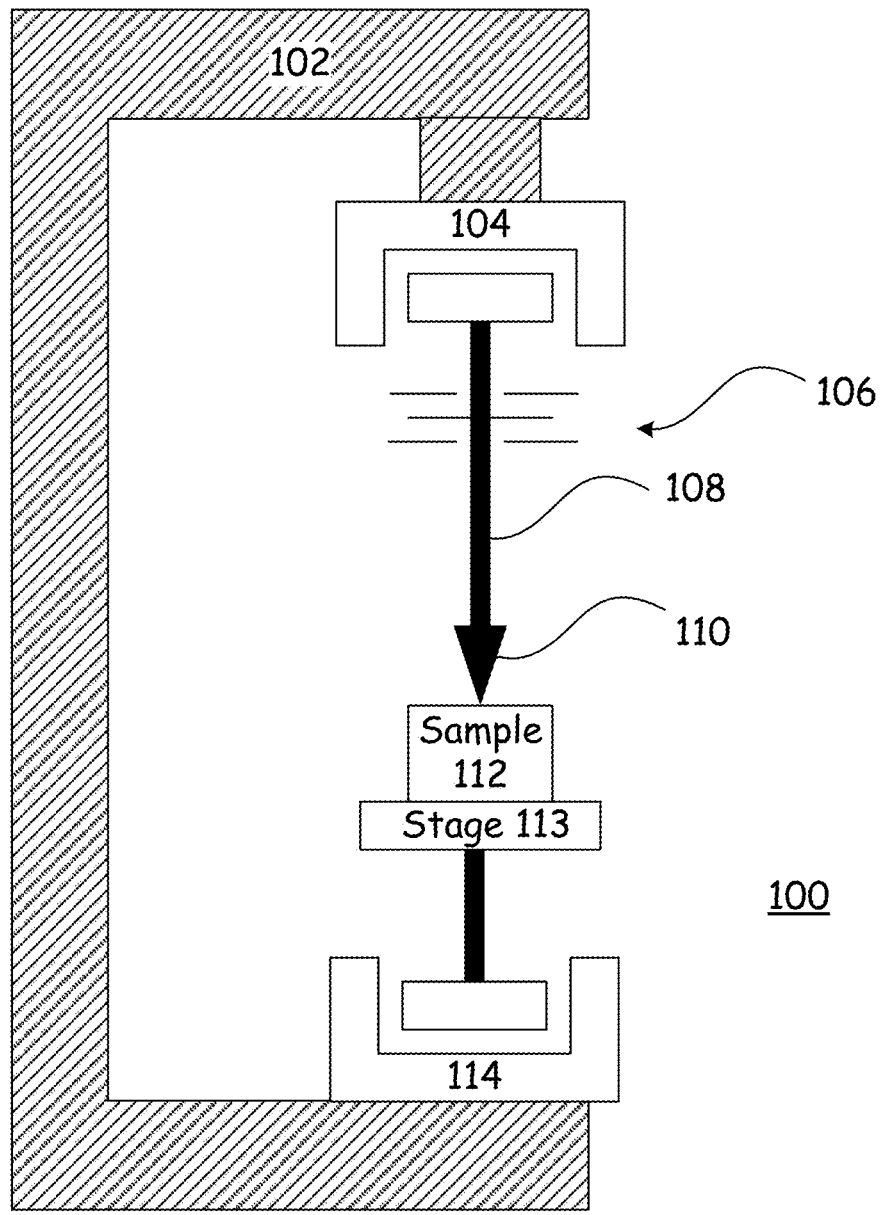
FIGS. 2-4 depict different locations for a compensating actuator on mechanical testing system according to embodiments of the present invention.
Figure 3:
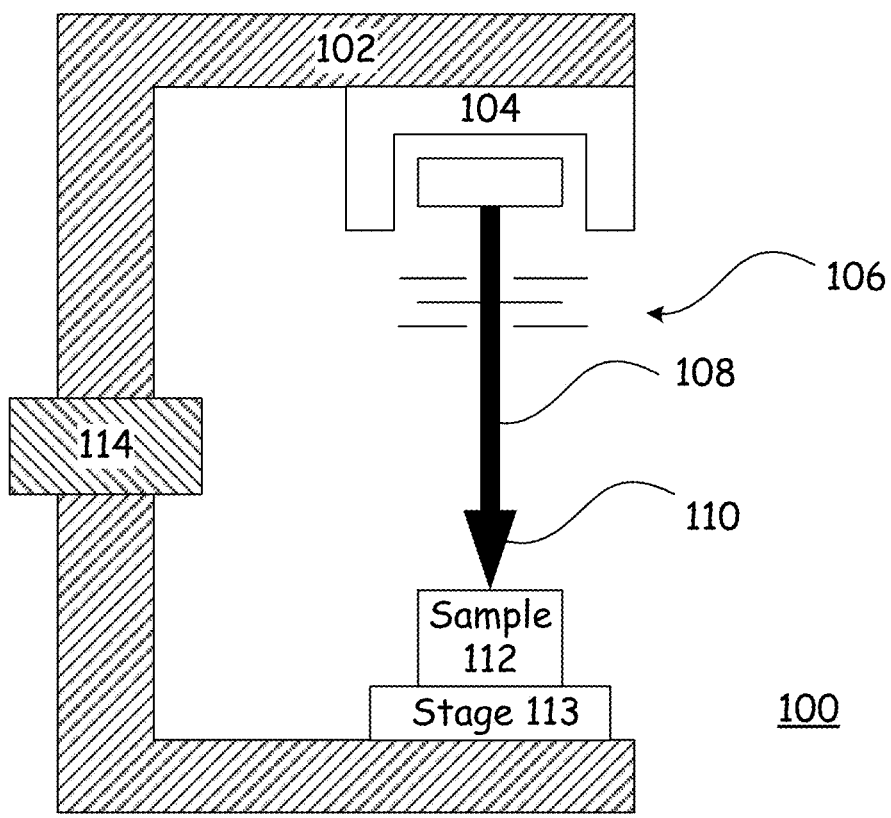
Figure 4:
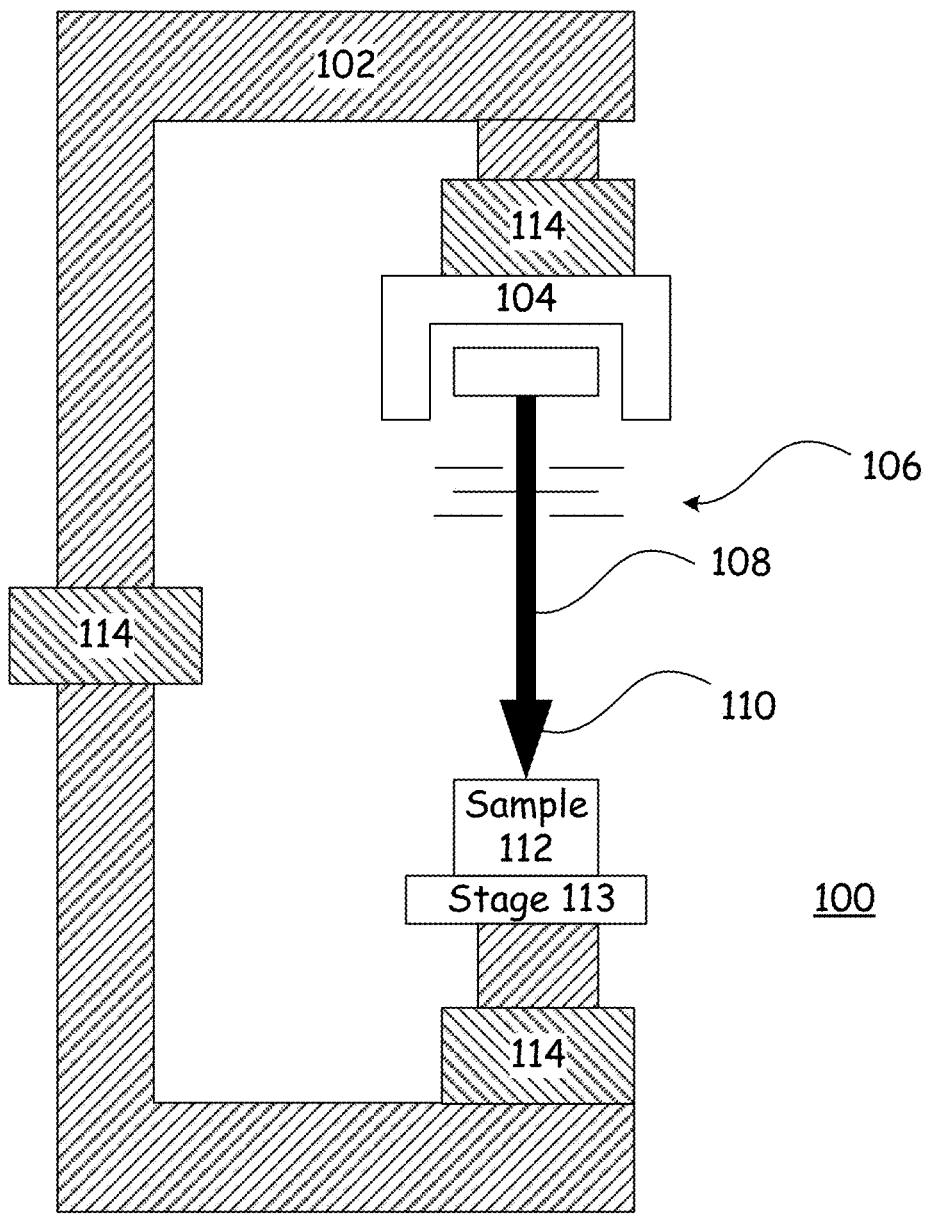

To compensate for these factors in the system 100, one or more compensating actuators 114 are placed somewhere within the circuit of the load frame 102. The purpose of the compensating actuator 114 is to apply a compensating force in an opposing direction to that which is applied by the primary actuator 104, such that the distance as measured by the displacement sensor 106 accurately reflects the actual distance that the tip 110 has penetrated into the surface of the sample 112. FIG. 2 shows a schematic representation of one configuration of the system 100 using mass, springs and dashpots.

The amount of force that is required to be exerted by the compensating actuator 114 is different, depending at least in part upon the construction of the mechanical testing system 100. The amount of compensating force that is required can be determined in various ways, such as empirically or theoretically or a combination of the two, for a given instrument, then written into the operational programming of the instrument 100. In some embodiments the compensating force that is applied by the compensating actuator or actuators 114 varies with the force that is applied by the primary actuator 104. In other embodiments the compensating force that is applied by the compensating actuator or actuators 114 is relatively uniform, regardless of the force that is applied by the primary actuator 104.

As built, most mechanical testing systems 100 have a frame 102 with an inherent stiffness of somewhere on the order of one to two million newtons per meter. Using the apparatus and method described herein, a frame 102 can be compensated to have an apparent stiffness of about tens of millions of newtons per meter, or more. However, in most applications, compensation to about ten million newtons per meter is adequate to reduce the errors in the hardness and other mechanical property calculations to a relatively insignificant level.

The primary actuator 104 and the compensating actuators 114 can be electromagnetic, electrostatic, piezoelectric, hydraulic, mechanical, pneumatic, or so forth. A schematic of one possible configuration of the system 100 is shown in FIG. 1. It shows a primary actuator 104 and a compensating electromagnetic actuator 114, a displacement sensor 106, the load frame 102, tip 110, and the sample 112. The compensating force can be applied synchronously or asynchronously, statically or dynamically with respect to the primary actuator 104.

The foregoing description of embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A mechanical testing system, comprising:
a frame,
a stage for holding a sample,
a probe having a tip configured to push into and make an indentation in a surface of the sample,
a primary actuator connected to the frame for applying a primary force to the probe to push the tip into the surface of the sample,
a displacement sensor for measuring a displacement value including a distance traveled by the probe relative to the sample as the primary force is applied, and
one or more compensating actuators connected to the frame, the one or more compensating actuators for applying a compensating force that maintains a fixed relative displacement between a reference point in the displacement sensor and a point on the sample.

2. The mechanical testing system of claim 1, wherein the one or more compensating actuators comprise multiple compensating actuators disposed at different positions on the frame.

3. The mechanical testing system of claim 1, wherein the one or more compensating actuators are disposed on an opposite side of the stage from the primary actuator.

4. The mechanical testing system of claim 1, wherein the primary actuator is at least one of electromagnetic, electrostatic, piezoelectric, hydraulic, mechanical, and pneumatic.

5. The mechanical testing system of claim 1, wherein the one or more compensating actuators are at least one of electromagnetic, electrostatic, piezoelectric, hydraulic, mechanical, and pneumatic.

6. The mechanical testing system of claim 1, wherein the displacement sensor uses at least one of a capacitor and a laser to measure the displacement.

7. The mechanical testing system of claim 1, wherein the compensating force corrects an apparent stiffness of the frame to about ten million newtons per meter.

8. A mechanical testing system, comprising:
a frame,
a stage for holding a sample,
a probe having a tip configured to push into and make an indentation in a surface of the sample,
a primary actuator connected to the frame for applying a primary force to the probe to push the tip into the surface of the sample, wherein the primary actuator is at least one of electromagnetic, electrostatic, piezoelectric, hydraulic, mechanical, and pneumatic,
a displacement sensor for measuring a displacement value including a distance traveled by the probe into the sample as the primary force is applied, and
a plurality of compensating actuators connected to the frame, the plurality of compensating actuators for applying a compensating force that maintains a fixed relative displacement between a reference point in the displacement sensor and a point on the sample, wherein the compensating force corrects an apparent stiffness of the frame to about ten million newtons per meter.

9. The mechanical testing system of claim 8, wherein the plurality of compensating actuators are at least one of electromagnetic, electrostatic, piezoelectric, hydraulic, mechanical, and pneumatic.

10. The mechanical testing system of claim 8, wherein the displacement sensor uses at least one of a capacitor and a laser to measure the displacement.

11. A method for testing at least one of a hardness and an elastic modulus of a sample, the method comprising the steps of:
placing a sample to be tested on a stage that is supported by a frame,
using a primary actuator that is supported by the frame to apply a primary force to drive a tool into a surface of the sample,
measuring a displacement value with a displacement sensor while applying a compensating force with a compensating actuator that is supported by the frame, where the compensating force maintains a fixed relative displacement between a reference point in the displacement sensor and a point on the sample, and
using the displacement value to calculate at least one of the hardness and the elastic modulus of the sample.

12. The method of claim 11, wherein the compensating actuator comprises multiple compensating actuators disposed at different positions on the frame.

13. The method of claim 11, wherein the compensating actuator is disposed on an opposite side of the stage from the primary actuator.

14. The method of claim 11, wherein the primary actuator is at least one of electromagnetic, electrostatic, piezoelectric, hydraulic, mechanical, and pneumatic.

15. The method of claim 11, wherein the compensating actuator is at least one of electromagnetic, electrostatic, piezoelectric, hydraulic, mechanical, and pneumatic.

16. The method of claim 11, wherein the displacement sensor uses at least one of a capacitor and a laser to measure the displacement.

17. The method of claim 11, wherein the compensating force corrects an apparent stiffness of the frame to about ten million newtons per meter.

* * * * *